United States Patent
Frey et al.

(10) Patent No.: US 10,471,368 B1
(45) Date of Patent: Nov. 12, 2019

(54) PROCESS FOR SEPARATION OF PROPYLENE FROM A LIQUEFIED PETROLEUM GAS STREAM

(71) Applicant: UOP LLC, Des Plaines, IL (US)

(72) Inventors: Stanley J. Frey, Palatine, IL (US); Chunqing Liu, Arlington Heights, IL (US); Trung Pham, Mount Prospect, IL (US)

(*) Notice: Subject to any disclaimer, the term of this patent is extended or adjusted under 35 U.S.C. 154(b) by 0 days.

(21) Appl. No.: 16/023,431

(22) Filed: Jun. 29, 2018

(51) Int. Cl.
| | |
|---|---|
| B01D 3/14 | (2006.01) |
| B01D 61/36 | (2006.01) |
| C07C 7/04 | (2006.01) |
| C07C 7/144 | (2006.01) |
| C07C 11/06 | (2006.01) |
| C07C 9/08 | (2006.01) |
| C07C 11/08 | (2006.01) |
| C07C 9/10 | (2006.01) |

(52) U.S. Cl.
CPC .......... *B01D 3/145* (2013.01); *B01D 61/364* (2013.01); *C07C 7/04* (2013.01); *C07C 7/144* (2013.01); *C07C 9/08* (2013.01); *C07C 11/06* (2013.01); *B01D 2256/24* (2013.01); *B01D 2257/7022* (2013.01); *C07C 9/10* (2013.01); *C07C 11/08* (2013.01)

(58) Field of Classification Search
CPC ................. B01D 3/145; B01D 61/364; B01D 2257/7022; B01D 2256/24; C07C 9/08; C07C 9/10; C07C 7/04; C07C 7/144; C07C 11/06; C07C 11/08
See application file for complete search history.

(56) References Cited

U.S. PATENT DOCUMENTS

| | | | |
|---|---|---|---|
| 2004/0182786 A1* | 9/2004 | Colling | B01D 3/14 210/640 |
| 2011/0049051 A1* | 3/2011 | Cougard | C07C 7/04 210/640 |
| 2015/0005459 A1* | 1/2015 | Janssens | C08F 6/001 526/68 |

* cited by examiner

Primary Examiner — In Suk C Bullock
Assistant Examiner — Jason Y Chong (57) ABSTRACT

The present invention relates to a combined C3/C4 splitter with a membrane system. More specifically, the present invention relates to a combined C3/C4 splitter column to separate highly pure propylene product from a liquefied petroleum gas stream, which eliminates a C3 splitter having over 120 trays and the additional equipment that a C3 splitter requires.

17 Claims, 9 Drawing Sheets

PROCESS FOR SEPARATION OF PROPYLENE FROM A LIQUEFIED PETROLEUM GAS STREAM

FIELD

The present invention relates to a combined C3/C4 splitter with a membrane system. More specifically, the present invention relates to a combined C3/C4 splitter column to separate a highly pure propylene product from a liquefied petroleum gas stream, which eliminates a C3 splitter having over 120 equilibrium trays and the additional equipment that a C3 splitter requires.

BACKGROUND

Membrane technology has been studied in the past to produce polymer grade propylene. For example, there are inventions that relate to installing a membrane module at the overhead of the C3 splitter. Other innovations also investigated integrating membranes around the C3 splitter. However, the one column that cannot be eliminated with any combination of membranes is the C3/C4 splitter because the membrane cannot perform carbon number separation. Therefore, it is advantageous to leverage the C3/C4 splitter as much as possible to minimize the membrane section and overall cost. It is feasible to use a C3/C4 splitter in combination with membranes to produce polymer grade propylene.

SUMMARY

In one embodiment of the invention is a process, comprising passing a feed stream to a column to produce a first overhead stream and a product stream; passing a first portion of the overhead stream back to the column and passing the second portion of the overhead stream to a splitter to produce a first stream and a second stream; passing the first stream to a stripper to produce a stripper overhead stream and a stripper product stream and passing the second stream to a membrane unit with the stripper overhead stream; and passing a retentate stream from the membrane unit back to the stripper and passing a permeate stream from the membrane unit to produce a polymer grade propylene stream.

In another embodiment of the invention is a process, comprising passing a feed stream to a dividing wall column to produce an overhead stream; flashing the overhead stream to produce a net gas stream; a first side draw stream; a second side draw stream, on the opposite side of the dividing wall from the feed; and a product stream; passing a first portion of the overhead residual stream back to the column; passing the first side draw stream to a treatment unit to produce a treated stream; passing a first portion of the second side draw stream back to the column and passing the second portion of the second side draw stream as a propane product; passing the treated stream to a membrane unit; and passing a retentate stream from the membrane unit back to the dividing wall column and passing a permeate stream from the membrane unit to produce a polymer grade propylene stream.

In yet another embodiment of the invention is a process, comprising passing a feed stream to a dividing wall column to produce a first overhead stream, a side draw stream and a product stream; passing at least a portion of the overhead stream to a heat pumped reboiling section to produce a heat pumped product stream; passing the heat pumped product stream to a membrane unit; passing a retentate stream from the membrane unit back to the dividing wall column and passing a permeate stream from the membrane unit to produce a polymer grade propylene stream.

In the foregoing, all temperatures are set forth in degrees Celsius and, all parts and percentages are by weight, unless otherwise indicated. Other objects, advantages and applications of the present invention will become apparent to those skilled in the art from the following detailed description and drawing. Additional objects, advantages and novel features of the examples will be set forth in part in the description which follows, and in part will become apparent to those skilled in the art upon examination of the following description and the accompanying drawing or may be learned by production or operation of the examples. The objects and advantages of the concepts may be realized and attained by means of the methodologies, instrumentalities and combinations particularly pointed out in the appended claims.

Definitions

As used herein, the term "stream", "feed", "product", "part" or "portion" can include various hydrocarbon molecules, such as straight-chain, branched, or cyclic alkanes, alkenes, alkadienes, and alkynes, and optionally other substances, such as gases, e.g., hydrogen, or impurities, such as heavy metals, and sulfur and nitrogen compounds. Each of the above may also include aromatic and non-aromatic hydrocarbons.

Hydrocarbon molecules may be abbreviated C1, C2, C3, Cn where "n" represents the number of carbon atoms in the one or more hydrocarbon molecules or the abbreviation may be used as an adjective for, e.g., non-aromatics or compounds. Similarly, aromatic compounds may be abbreviated A6, A7, A8, An where "n" represents the number of carbon atoms in the one or more aromatic molecules. Furthermore, a superscript "+" or "−" may be used with an abbreviated one or more hydrocarbons notation, e.g., C3+ or C3−, which is inclusive of the abbreviated one or more hydrocarbons. As an example, the abbreviation "C3+" means one or more hydrocarbon molecules of three or more carbon atoms.

As used herein, the term "zone" can refer to an area including one or more equipment items and/or one or more sub-zones. Equipment items can include, but are not limited to, one or more reactors or reactor vessels, separation vessels, distillation towers, heaters, exchangers, pipes, pumps, compressors, and controllers. Additionally, an equipment item, such as a reactor, dryer, or vessel, can further include one or more zones or sub-zones.

Equilibrium trays are conventionally numbered in ascending fashion from top of the column to the bottom with the top tray (lowest temperature) being equilibrium tray number 1. An equilibrium tray (or alternatively termed "stage") is understood by those skilled in the art of distillation design but to be certain of the definition we refer to that given in Treybal, RE, Mass Transfer Operations, $3^{rd}$ Edition, McGraw-Hill Book Company, NY, NY, 1980, Pg 10 as a stage as one where the effluent phases are in equilibrium, so that a longer time of contact will bring about no additional change of composition. Associated with that is the definition of stage efficiency as the fraction of the distance of the approach to that equilibrium for the entering feed phases.

DETAILED DESCRIPTION

The following detailed description is merely exemplary in nature and is not intended to limit the application and uses of the embodiment described. Furthermore, there is no intention to be bound by any theory presented in the preceding background or the following detailed description.

The description of the apparatus of this invention is presented with reference to the attached FIGURES. The FIGURES are a simplified diagrams of the preferred embodiments of this invention and is not intended as an undue limitation on the generally broad scope of the description provided herein and the appended claims. Certain hardware such as valves, pumps, compressors, heat exchangers, instrumentation and controls, have been omitted as not essential to a clear understanding of the invention. The use and application of this hardware is well within the skill of the art.

Figure 1:
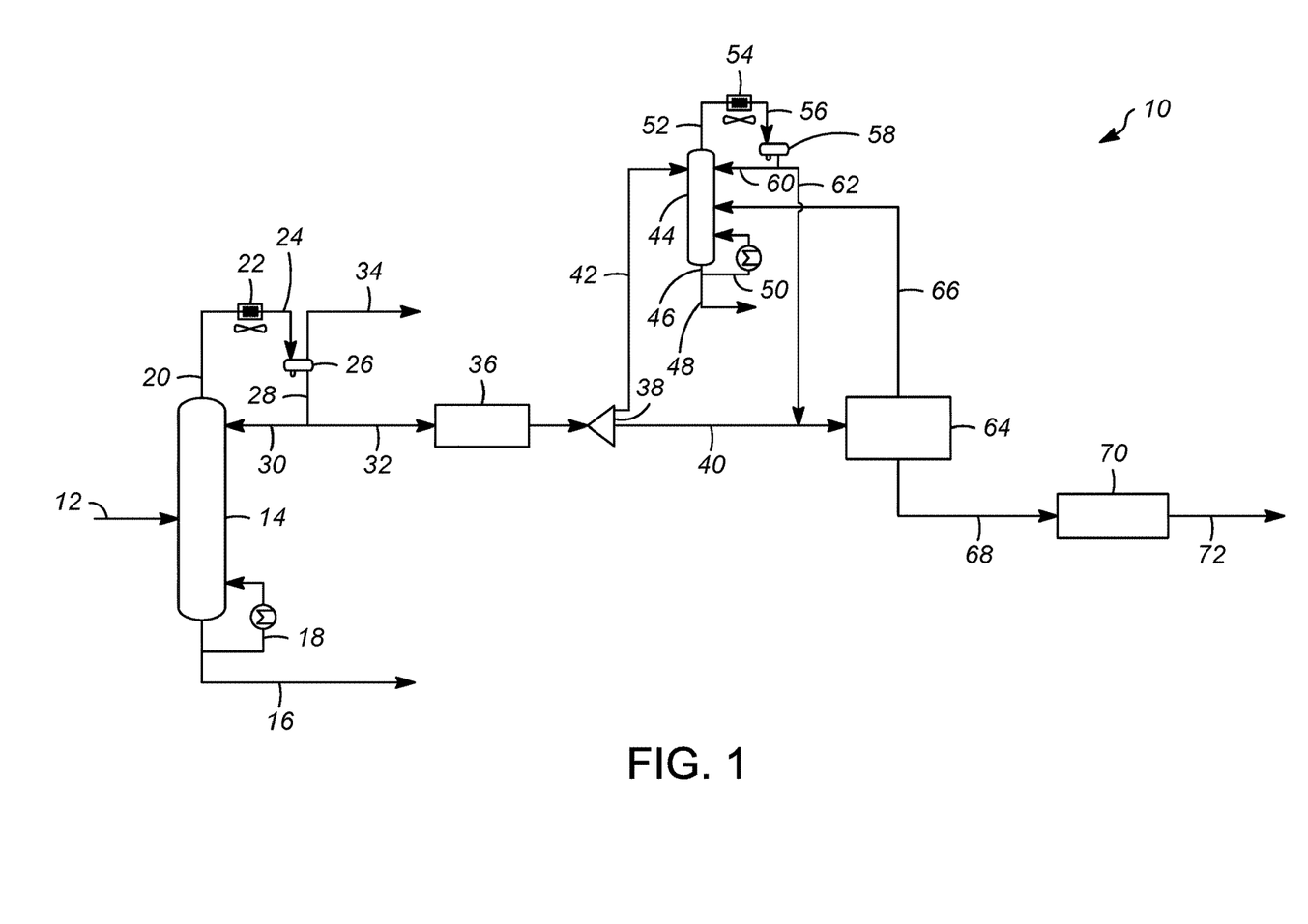
FIG. 1 illustrates an example of a combined C3/C4 splitter with a membrane system.

As shown in FIG. 1, a process 10 wherein a stream 12 enters a column 14. Stream 12 may be a treated LPG stream from a caustic mercaptan oxidation process. The column produces an overhead stream 20 and a bottoms stream 16. A portion of the bottoms stream 16 is sent to the butane product and another portion of the bottoms stream 18 is sent back to the column. The overhead stream 20 is sent to a column overhead condenser 22. Stream 24 leaves the column overhead condenser and is sent to a receiver 26 which produces an off gas stream 34 and a liquid stream 28. A portion of the liquid stream 28 is sent in line 30 back to the column 14, and another portion of the liquid stream 28 is sent in line 32 to a treatment section 36. The product from the treatment section 36 is divided in a flow splitter device 38 producing stream 42 and stream 40. Stream 42 is sent to a column 44 and stream 40 is sent to a membrane unit 64. Stream 42 enters the near the top of the column 44 and produces an overhead stream 52 and a bottoms stream 46. The overhead stream 52 is sent to a condenser 54 which produces stream 56 which is sent to receiver 58 which produces stream 60 which is sent back to the column 44 and stream 62 which is sent to be combined with stream 40 before entering the membrane unit 64. The bottoms stream from the column 44 exits the column in line 46. A portion of line 46 is sent back to the column 44 in line 50 and a portion of the bottoms stream 46 is propane product in line 48 which optionally meets HD-5 product specification, with maximum propylene concentration of 5% by volume.

The membrane unit produces an overhead stream 66 which is sent back to column 44. The membrane unit may comprise a membrane as recently described in US 2017/0354918 A1; U.S. application Ser. No. 15/615,134 filed Jun. 6, 2017; and U.S. Provisional Application No. 62/549,820 filed Aug. 24, 2017 incorporated herein in their entireties. The membrane unit may comprise a plurality of membranes wherein said membranes are facilitated transport membranes comprising a nanoporous support membrane, a hydrophilic polymer inside the nanopores on the skin layer surface of the support membrane, a thin, nonporous, hydrophilic polymer layer coated on the surface of the support membrane, and metal salts incorporated in the hydrophilic polymer layer coated on the surface of the support membrane and the hydrophilic polymer inside the nanopores. The membrane unit operates at about 30-80° C., preferably at about 45-65° C., under 80-300 psig feed pressure, preferably under 100-240 psig feed pressure, with a humidity level at 40-100%, preferably at 50-90%. Sufficient water vapor is added to the combined stream from stream 40 and stream 62 before the stream contacts the membrane unit so that the stream has from 40 to 100% humidity and more typically has from 50-90% humidity. The impurities that are removed from the combined stream before entering the membrane unit in the present invention include arsine, phosphine, sulfur compounds, caustic water, methyl acetylene, and propadiene.

The facilitated transport membrane disclosed in US 2017/0354918 A1 comprising a nanoporous support membrane, a hydrophilic polymer inside the nanopores on the skin layer surface of the support membrane, a thin, nonporous, hydrophilic polymer layer coated on the surface of the support membrane, and metal salts incorporated in the hydrophilic polymer layer coated on the surface of the support membrane and the hydrophilic polymer inside the nanopores can be used as the membranes in the membrane unit described in the present invention. The nanoporous support membrane used for the preparation of the facilitated transport membrane comprising a nanoporous support membrane, a hydrophilic polymer inside the nanopores on the surface of the support membrane, a thin, nonporous, hydrophilic polymer layer coated on the surface of said support membrane, and metal salts incorporated in the hydrophilic polymer layer coated on the surface of the support membrane and said hydrophilic polymer inside the nanopores used in the present invention comprises a polymer selected from a group consisting of, but is not limited to, polyethersulfone (PES), a blend of PES and polyimide, cellulose acetate, cellulose triacetate, and a blend of cellulose acetate and cellulose triacetate. The nanoporous support membrane used in the current invention has an average pore diameter of less than 10 nm on the membrane skin layer surface. The nanoporous support membrane used in the current invention can be either asymmetric integrally skinned membrane or thin film composite (TFC) membrane with either flat sheet (spiral wound) or hollow fiber geometry. The hydrophilic polymer inside the nanopores on the surface of the nanoporous support membrane of the facilitated transport membrane described in US 2017/0354918 A1 can be selected from, but is not limited to, a group of hydrophilic polymers containing chitosan, sodium carboxylmethyl-chitosan, carboxylmethyl-chitosan, hyaluronic acid, sodium hyaluronate, carbopol, polycarbophil calcium, poly(acrylic acid) (PAA), poly (methacrylic acid) (PMA), sodium alginate, alginic acid, poly(vinyl alcohol) (PVA), poly(ethylene oxide) (PEO), poly(ethylene glycol) (PEG), poly(vinylpyrrolidone) (PVP), gelatin, carrageenan, sodium lignosulfonate, and mixtures thereof. The metal salts incorporated in the hydrophilic polymer layer coated on the surface of said support membrane and the hydrophilic polymer inside the nanopores of the facilitated transport membrane described in US 2017/

0354918 A1 are preferred to be selected from silver salts or copper salts, such as silver(I) nitrate or copper(I) chloride. The dried nanoporous support membrane comprising hydrophilic polymers inside the nanopores on the membrane surface described in US 2017/0354918 A1 has carbon dioxide permeance of 800-10,000 GPU and no carbon dioxide/methane selectivity at 50° C. under 30-100 psig 10% $CO_2$/90% $CH_4$ mixed gas feed pressure.

The facilitated transport membrane disclosed in U.S. application Ser. No. 15/615,134 comprising a nanoporous polyethersulfone/polyvinylpyrrolidone blend support membrane, a hydrophilic polymer inside nanopores of said support membrane, a hydrophilic polymer coating layer on a surface of the support membrane and metal salts in said hydrophilic polymer coating layer and in said hydrophilic polymer inside said nanopores of said support membrane can also be used as the membranes in the membrane unit described in the present invention.

The membrane disclosed in U.S. Provisional Application No. 62/549,820 comprising a polyethersulfone/polyethylene oxide-polysilsesquioxane blend support membrane comprising a polyethylene oxide-polysilsesquioxane polymer and a polyethersulfone polymer; a hydrophilic polymer inside the pores on the skin layer surface of the polyethersulfone/polyethylene oxide-polysilsesquioxane blend support membrane; a hydrophilic polymer coated on the skin layer surface of the polyethersulfone/polyethylene oxide-polysilsesquioxane blend support membrane, and metal salts incorporated in the hydrophilic polymer coating layer and the skin layer surface pores of the polyethersulfone/polyethylene oxide-polysilsesquioxane blend support membrane can also be used as the membranes in the membrane unit described in the present invention.

The permeate stream 68 is optionally sent to a compression and cooling unit 70 to produce a liquid propylene stream. The compression and cooling unit 70 produces stream 72 which may contain about 99.5% polymer grade propylene.

Figure 2:
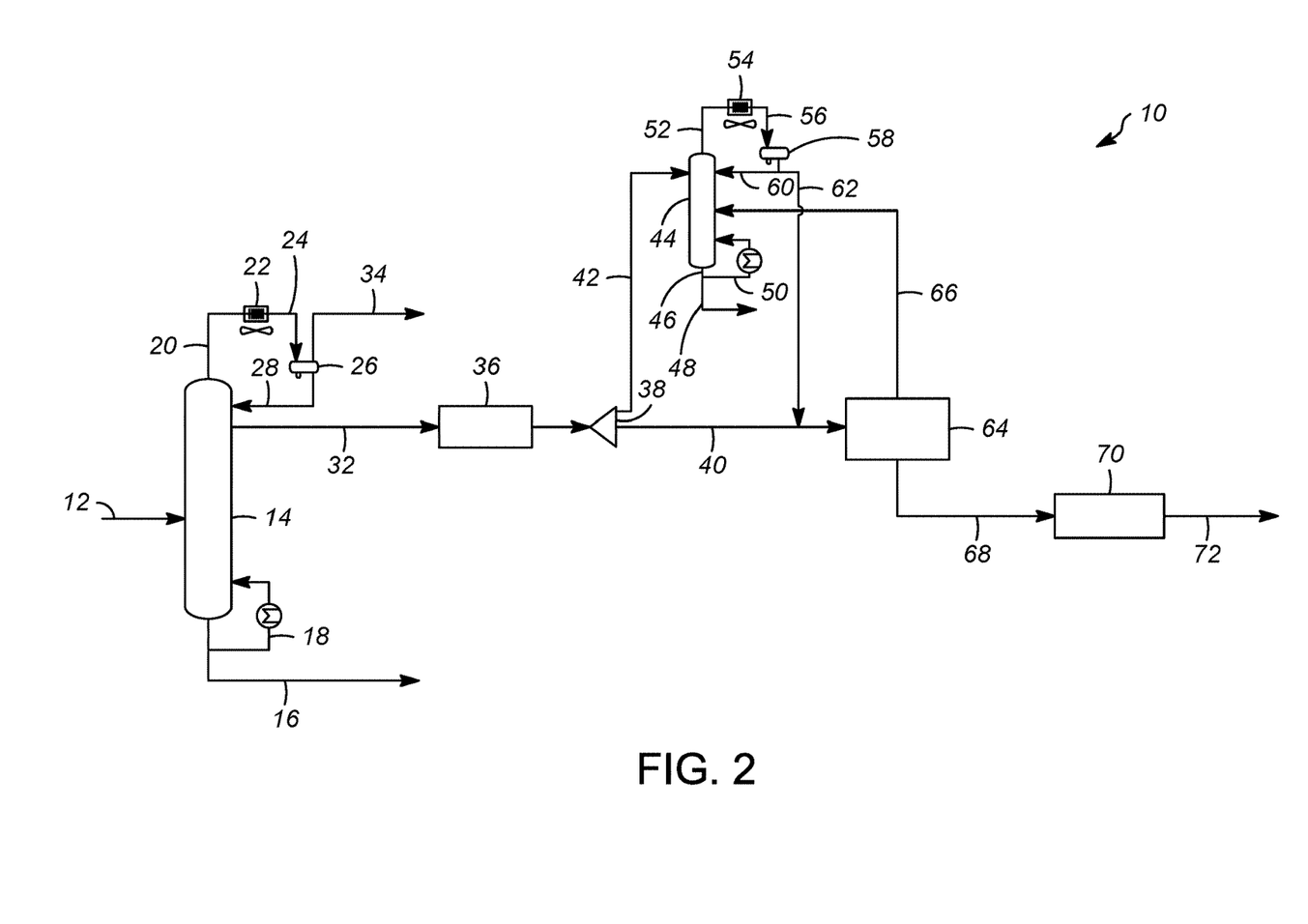
FIG. 2 illustrates an example of a combined C3/C4 splitter with a membrane system.

Now turning to FIG. 2, the overall flow scheme 10 is similar to that of FIG. 1, however in FIG. 2, a propylene stream 32 is taken from the column 14 and taken directly to the treatment unit 36. In FIG. 2, streams 28 and 32 are separate, as opposed to FIG. 1, where stream 28 leaves the receiver 26, and a portion of the stream 28 goes back to the column 14 and a portion of the stream 32 goes to the treatment unit 36. FIG. 2 is similar to FIG. 1, except that C3/C4 splitter 14 in FIG. 2 includes a pasteurization section and a C2/non-condensable vent. The propylene stream 32 is a sidedraw liquid stream instead of an overhead distillate at the condenser stage. The pasteurization section may include 1-15 equilibrium trays, preferably 1-10 equilibrium trays. The pasteurization section is the top section of the column above which the propylene stream 32 is taken as a sidedraw liquid stream.

Figure 3:
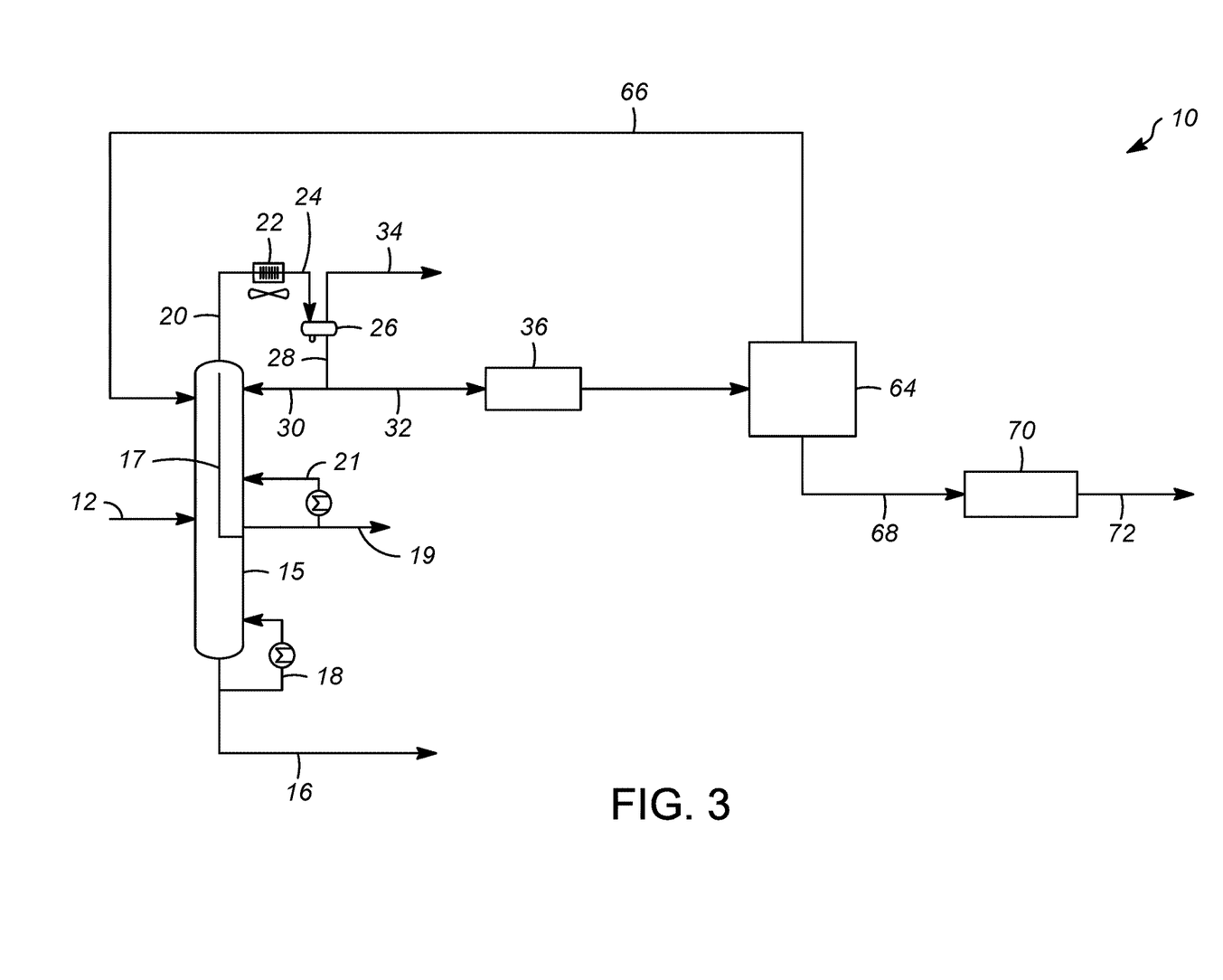
FIG. 3 illustrates an example of a combined C3/C4 splitter with a membrane system.

The example in FIG. 3 illustrates a C3/C4 splitter column 15 having a dividing wall 17 section at the top separating the feed side from the side draw liquid point. The overhead distillate 20 is a propylene rich stream comprising 60-95% propylene (C3=), or 65-80% C3=. A portion of the side draw liquid 19 is reboiled with an external reboiler 21 (for example one could use low pressure steam) and withdrawn as a propane product in stream 19 comprising 80-98% C3, or 92-96% C3. As illustrated in FIG. 3, at the end of the dividing wall 17, for the sidedraw product side, the bottom of this section is isolated from the bottom part of the C3/C4 splitter. The purpose is to prevent any C4 from coming into contact and creating inefficient mixing with the C3 rich portion already created by the dividing wall and to provide dedicated heating/reboiling zone for propane product. The dividing wall portion includes 20-45 equilibrium trays, or 25-40 equilibrium trays. The top of the wall location is 1-10 equilibrium trays, or 1-5 equilibrium trays from the top tray. The propylene distillate from the C3/C4 splitter overhead receiver stream 32 is contacted with the treatment unit 36 to remove contaminants as described earlier. The effluent after treatment is vaporized, heated to required membrane operation temperature (~30-80° C., or –45-65° C.), then combined with water vapor and contacted with a membrane unit 64 to separate a permeate product with high propylene concentration, 99.0-99.95 mol % C3=, or 99.2-99.6 mol % C3=. The retentate stream 66 from the membrane is contacted with the C3/C4 Splitter at a higher tray location than the LPG feed stream 12 and sidedraw product stream 19.

Figure 4:
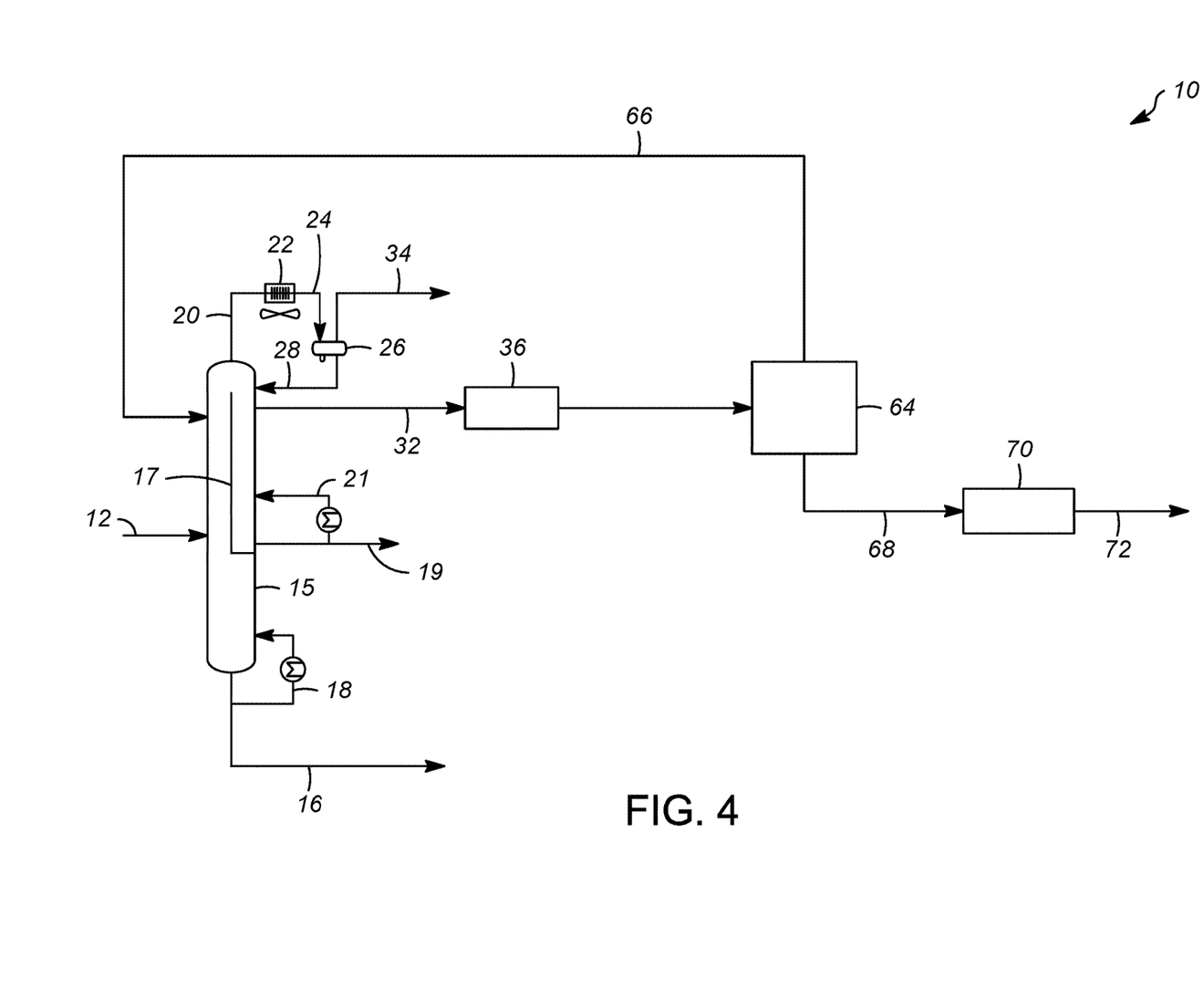
FIG. 4 illustrates an example of a combined C3/C4 splitter with a membrane system.

Now turning to FIG. 4, the overall flow scheme 10 is similar to that of FIG. 1, however in FIG. 4, a propylene stream 32 is taken from the column 15 and taken directly to the treatment unit 36. In FIG. 4, streams 28 and 32 are separate, as opposed to FIG. 1, where stream 28 leaves the receiver 26, and a portion of the stream 28 goes back to the column 15 and a portion of the stream 32 goes to the treatment unit 36. FIG. 4 is similar to FIG. 1, except that C3/C4 splitter 15 in FIG. 4 includes a pasteurization section and a C2/non-condensable vent. The propylene stream 32 is a sidedraw liquid stream instead of an overhead distillate at the condenser stage. The pasteurization section may include 1-15 equilibrium trays, preferably 1-10 equilibrium trays. The pasteurization section is the top section of the column below which the propylene stream 32 is taken as a sidedraw liquid stream.

Figure 5:
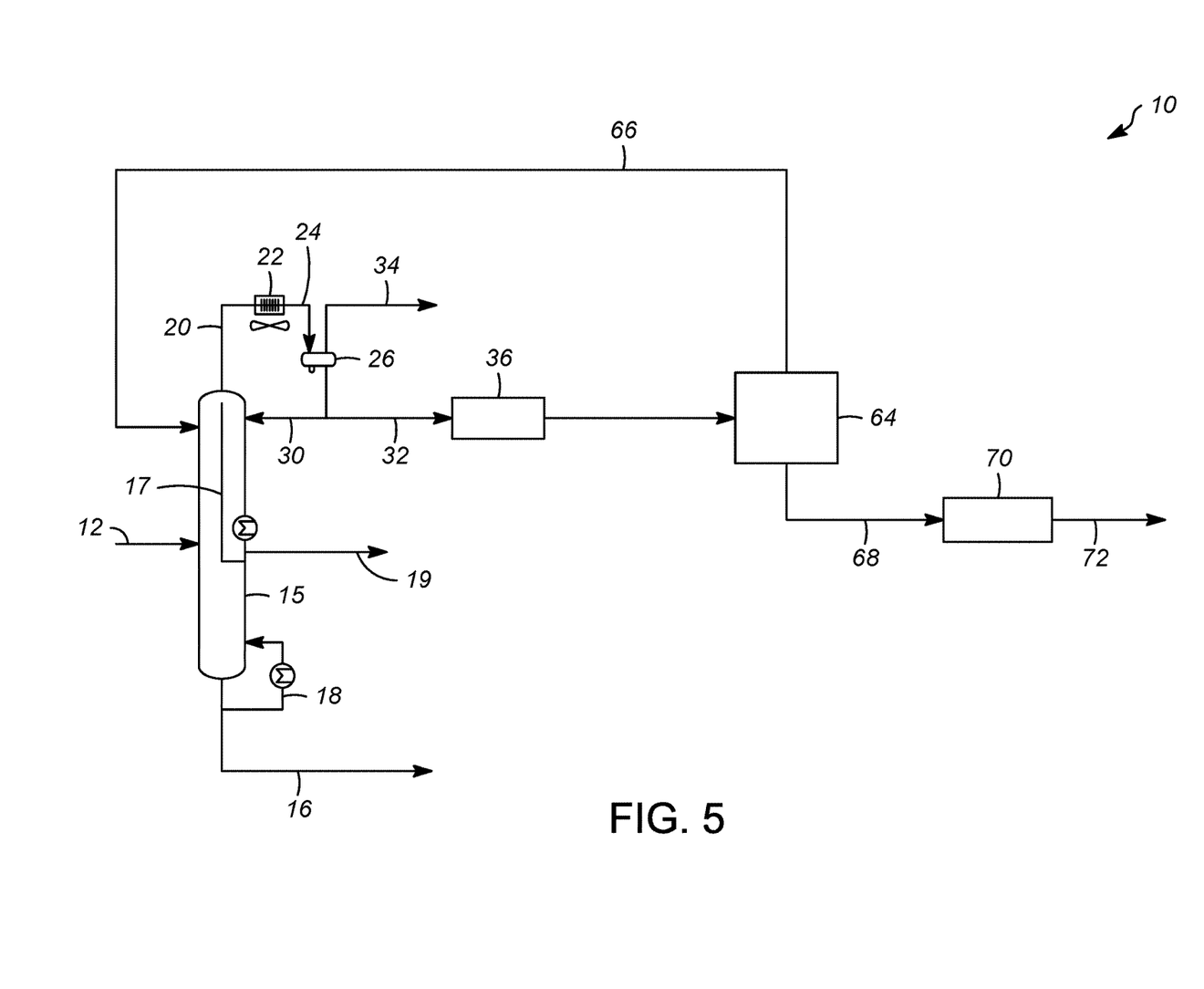
FIG. 5 illustrates an example of a combined C3/C4 splitter with a membrane system.

The example in FIG. 5 illustrates a C3/C4 splitter column 15 with a dividing wall 17 section at the top. The overhead distillate is a propylene rich stream 20 (60-95% C3=, or 65-80% C3=). One side of the wall at the bottom includes a stab-in reboiler 21 and the liquid sidedraw is propane product stream 19. The propane product stream 19 may comprise about 90-98% C3 or about 92-96% C3. Note that for the sidedraw product side, the bottom of the dividing wall section is isolated from the bottom part of the C3/C4 splitter as described in FIG. 3. The dividing wall height and location are the same as described earlier in FIG. 3. The propylene distillate from the overhead liquid stream 32 continues contacting with the treatment unit 36 followed by the membrane unit 64 to produce the final propylene product stream 72. The final propylene product stream may comprise about 99.0 to about 99.95 mol % C3= or about 99.2 to about 99.6 mol % C3=.

Figure 6:
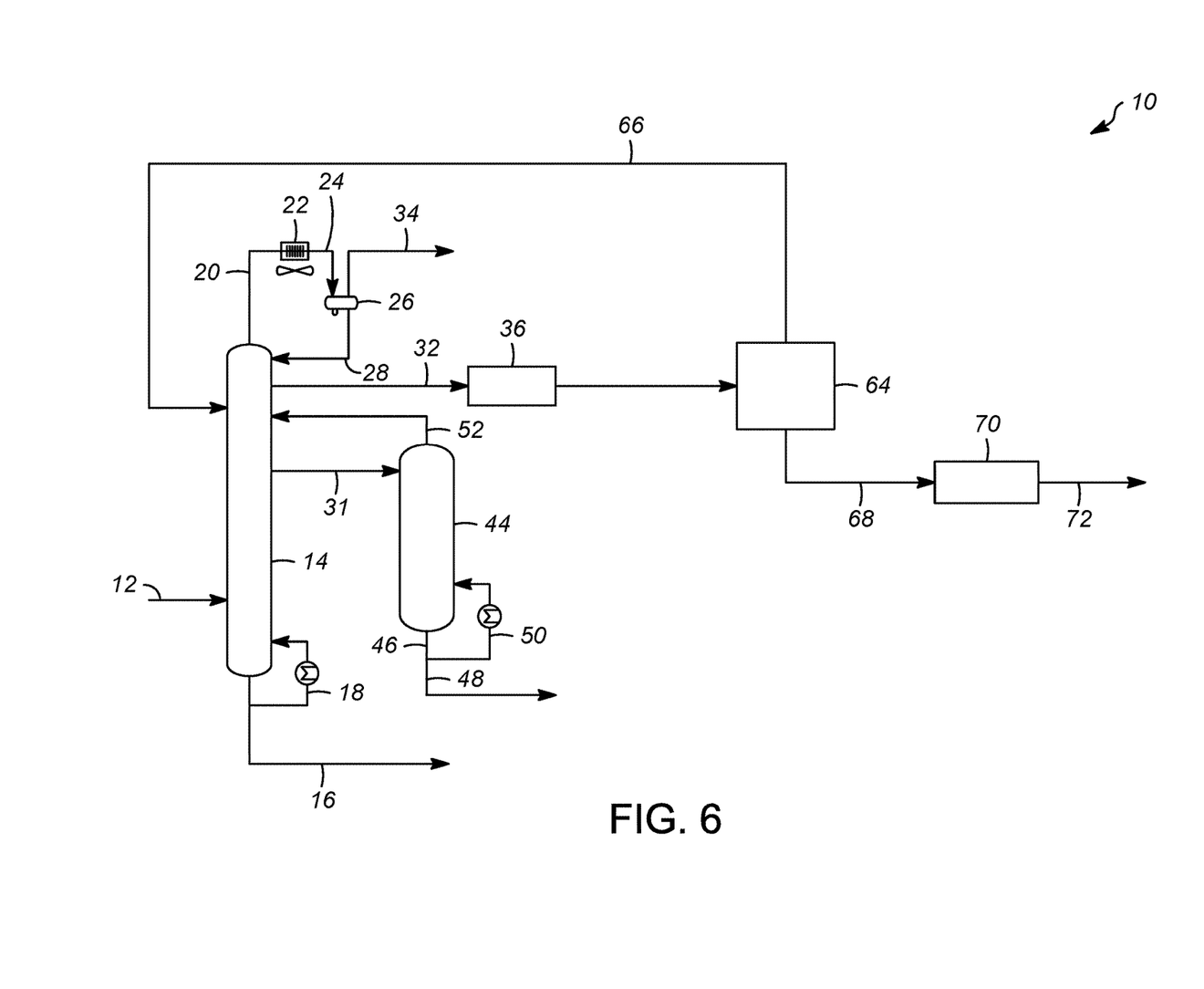
FIG. 6 illustrates an example of a combined C3/C4 splitter with a membrane system.

Now turning to FIG. 6, the process 10 includes a C3/C4 splitter column 14 with a side stripper including about 20 to about 45, or preferably about 25 to about 40 equilibrium trays. The side stripper is to remove propane product at the bottom (80-98% C3, or 92-96% C3). The side draw stream 31 location is located near the top of the splitter, at equilibrium tray 1-10, or 2-6. The propylene distillate from the overhead liquid stream 32 continues contacting with the treatment unit followed by the membrane unit to produce the final propylene product, 99.0-99.95 mol % C3=, or 99.2-99.6 mol % C3=. The side stripper reboiler also uses low pressure steam to reboil the stripper bottom liquid.

Figure 7:
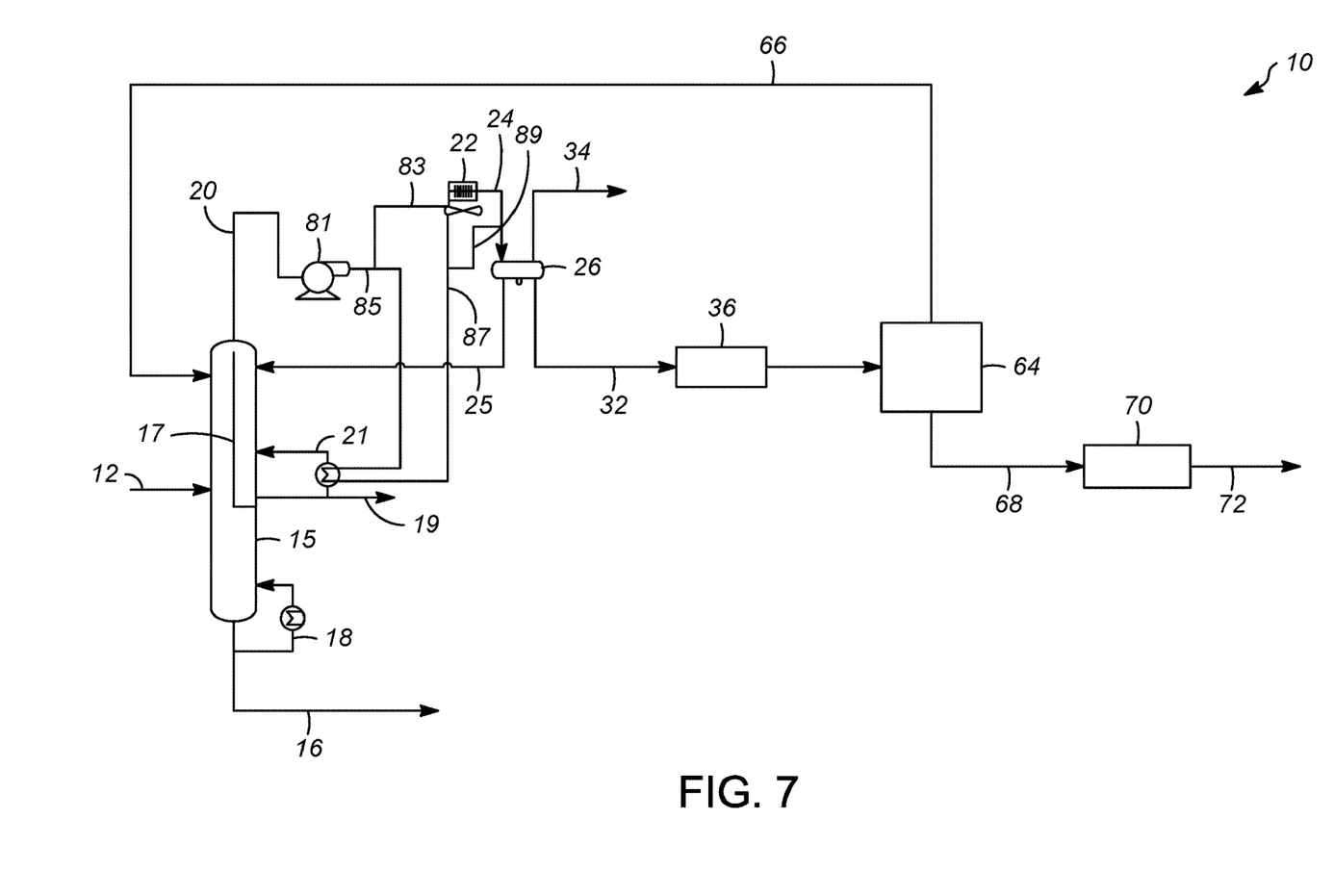
FIG. 7 illustrates an example of a combined C3/C4 splitter with a membrane system.

FIG. 7 illustrates the process using a heat pumped reboiler. The process can be improved by using heat pump compression (HPC) 81 providing heat to the reboiler of the side wall for propane outlet/separation. When using HPC, the C3/C4 splitter column 15 can be operated at a lower pressure. The column reflux ratio decreases, and reboiler duty also decreases. And the sidecut reboiler does not need external utility supply (steam or other heating medium).

In the heat pump compression (HPC) illustrated in FIG. 7, the C3/C4 column 15 can be run at about 80 psig to about 200 psig or preferably about 140 psig to about 180 psig. It should be noted that conventional C3/C4 splitters run at about 200 psig to about 300 psig, or about 230 psig about 280 psig with no HPC. The overhead vapor 20 can be compressed to about 230 psig to about 280 psig, or about 240 psig about 270 psig and a portion of the hot vapor 85 can reboil the side column (or parallel side) to remove a highly pure propane product (about 80% to about 98% C3, or about 94% to about 96% C3). The hot vapor 87 after reboiling the side draw liquid stream along with a remaining portion of the hot vapor 83 can be cooled with air-cooled or water-cooled exchanger and the mixed stream 89 is contacted with a receiver; the outlet of the receiver is split to two streams: a reflux stream 25 going back to the column and a liquid stream 32 which continues to the treatment section 36 and thereafter is heated/vaporized and mixed with a water stream before entering the membrane unit 64. The portion of the hot vapor 89 after reboiling the side column (or parallel side) is contacted directly with a receiver without cooling air-cooled or water-cooled exchanger.

With lower pressure operation for the C3/C4 splitter, the reflux ratio decreased from about 15 to about 20 to about 6 to about 10. The reboiler duty of the splitter also decreases by about 20% to about 32%, or about 24% to about 30%. Also, by running at lower pressure and reduced reflux ratio, the diameter of the column reduces by about 12% to about 25%, or about 15% to about 20%. The diameter of the side stripper also reduced by about 20% to about 35%, or 24% to about 32%. The lower pressure is also advantageous/favored for the side stripper inducing higher volatility split/separation for C3 components: propane and propylene. Alternatively the reduced load on the column trays, reboiler and, condenser can be exploited in revamps of existing C3/C4 splitters keep a more nearly constant tray loading for the two dividing wall segregation of sides in the column relative to the original loadings in the conventional C3/C4 splitter. It is important to note that the side reboiler no longer requires use of external heating medium such as low pressure steam or other source.

Figure 8:
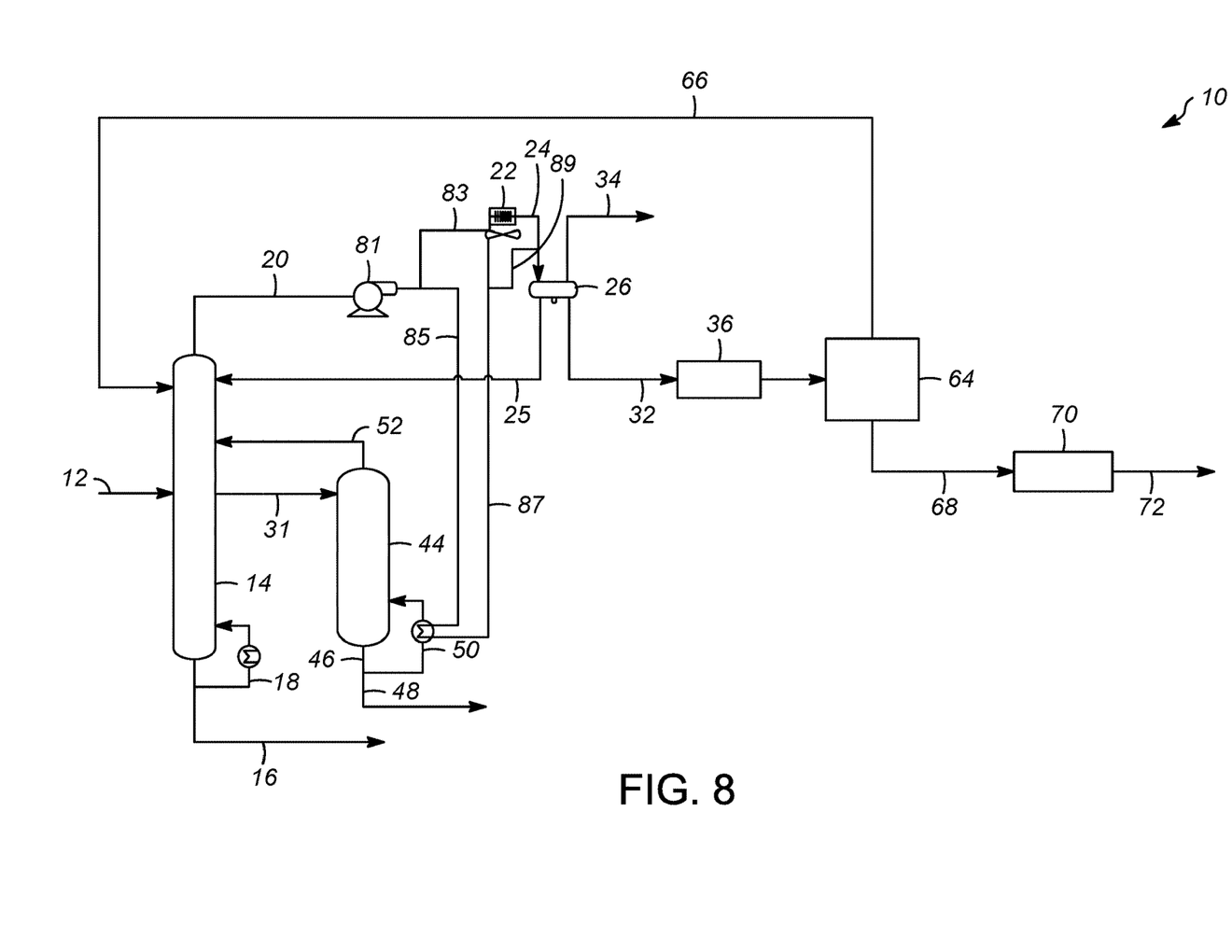
FIG. 8 illustrates an example of a combined C3/C4 splitter with a membrane system.

Now turning to FIG. 8, in another embodiment, a C3/C4 splitter with heat pump reboiler of FIG. 7 integrated with a C3 side stripper (for revamp, C3 side stripper could be an existing C3 splitter) of FIG. 6. Both of the columns can be run at lower pressure at about 80 psig to about 200 psig range, or preferably about 140 to about 180 psig. The overhead vapor from C3/C4 splitter is compressed providing reboiling heat to the C3 side stripper bottoms. Note that for revamp cases, where C3 splitter has a heat pump compressor at the overhead of the column, this compressor can be re-routed/connected to the overhead of the C3/C4 splitter for the integration of the 2 columns with the membrane unit. This revamp scenario opens up increased capacity/debottleneck the 2 columns from about 10% to about 50% more capacity, or about 20% to about 40% more capacity.

Figure 9:
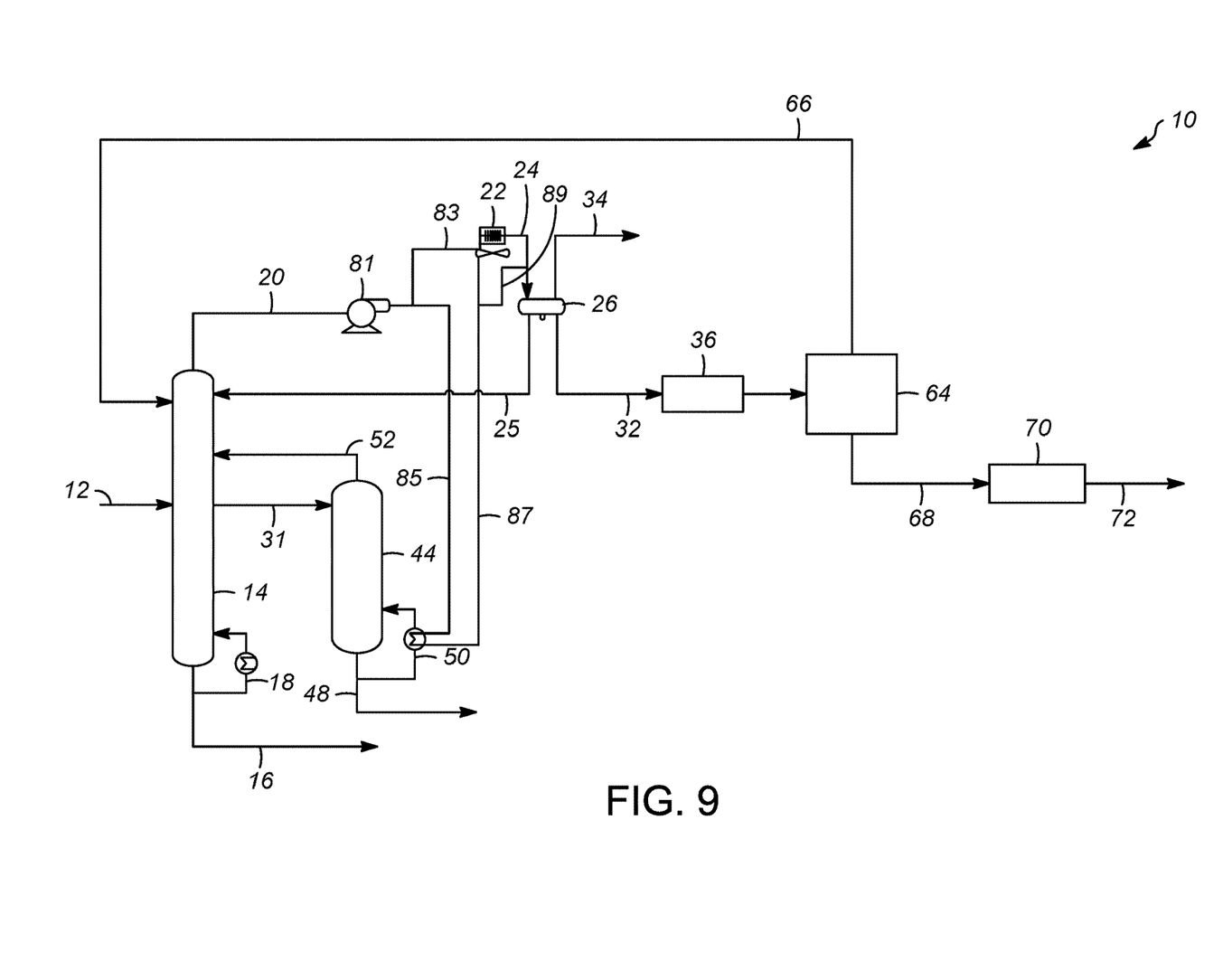
FIG. 9 illustrates an example of a combined C3/C4 splitter with a membrane system.

Finally, FIG. 9 illustrates a variation of FIG. 8 C3/C4 splitter with the top part, 5-12 additional trays, as the pasteurization section for better separation of trace C2 components (might be present in the feed to the C3/C4 splitter). The heat pump compressor is installed at the top overhead of the column. And a side draw liquid stream (propylene rich) is withdrawn below the pasteurization section and contacted with the treatment unit followed by the membrane unit.

Any of the above lines, conduits, units, devices, vessels, surrounding environments, zones or similar may be equipped with one or more monitoring components including sensors, measurement devices, data capture devices or data transmission devices. Signals, process or status measurements, and data from monitoring components may be used to monitor conditions in, around, and on process equipment. Signals, measurements, and/or data generated or recorded by monitoring components may be collected, processed, and/or transmitted through one or more networks or connections that may be private or public, general or specific, direct or indirect, wired or wireless, encrypted or not encrypted, and/or combination(s) thereof; the specification is not intended to be limiting in this respect.

Signals, measurements, and/or data generated or recorded by monitoring components may be transmitted to one or more computing devices or systems. Computing devices or systems may include at least one processor and memory storing computer-readable instructions that, when executed by the at least one processor, cause the one or more computing devices to perform a process that may include one or more steps. For example, the one or more computing devices may be configured to receive, from one or more monitoring component, data related to at least one piece of equipment associated with the process. The one or more computing devices or systems may be configured to analyze the data. Based on analyzing the data, the one or more computing devices or systems may be configured to determine one or more recommended adjustments to one or more parameters of one or more processes described herein. The one or more computing devices or systems may be configured to transmit encrypted or unencrypted data that includes the one or more recommended adjustments to the one or more parameters of the one or more processes described herein.

While the invention has been described with what are presently considered the preferred embodiments, it is to be understood that the invention is not limited to the disclosed embodiments, but it is intended to cover various modifications and equivalent arrangements included within the scope of the appended claims.

SPECIFIC EMBODIMENTS

While the following is described in conjunction with specific embodiments, it will be understood that this description is intended to illustrate and not limit the scope of the preceding description and the appended claims.

A first embodiment of the invention is a process, comprising passing a feed stream to a column to produce a first overhead stream and a product stream; passing a first portion of the overhead stream back to the column and passing the second portion of the overhead stream to a splitter to produce a first stream and a second stream; passing the first stream to a stripper to produce a stripper overhead stream and a stripper product stream and passing the second stream to a membrane unit with the stripper overhead stream; and passing a retentate stream from the membrane unit back to the stripper and passing a permeate stream from the membrane unit to produce a polymer grade propylene stream. An embodiment of the invention is one, any or all of prior embodiments in this paragraph up through the first embodiment in this paragraph, wherein the feed stream may be a treated liquid petroleum gas stream from a caustic mercaptan oxidation process. An embodiment of the invention is one, any or all of prior embodiments in this paragraph up through the first embodiment in this paragraph, wherein the column comprises about 40 to about 80 trays, preferably about 50 to about 70 trays. An embodiment of the invention is one, any or all of prior embodiments in this paragraph up through the first embodiment in this paragraph, wherein the membrane unit comprises a plurality of membranes wherein the membranes are facilitated transport membranes comprising a nanoporous support membrane, a hydrophilic polymer inside the nanopores on the skin layer surface of the support membrane, a thin, nonporous, hydrophilic polymer layer coated on the surface of the support membrane, and metal salts incorporated in the hydrophilic polymer layer coated on the surface of the support membrane and the hydrophilic polymer inside the nanopores. An embodiment of the invention is one, any or all of prior embodiments in this paragraph up through the first embodiment in this paragraph, wherein the membrane unit operates at about 30-80° C., preferably at about 45-65° C., under 80-300 psig feed pressure, preferably under 100-240 psig feed pressure, with a humidity level at 40-100%, preferably at 50-90%. An embodiment of the invention is one, any or all of prior embodiments in this paragraph up through the first embodiment in this paragraph, further comprising the side draw stream passed through a treatment unit where contaminants are removed. An embodiment of the invention is one, any or all of prior embodiments in this paragraph up through the first embodiment in this paragraph, further comprising at least one of sensing at least one parameter of the process and generating a signal or data from the sensing; generating and transmitting a signal; or generating and transmitting data, wherein the splitter fraction is controlled or varied based on the composition signal feedback obtained from the feed stream to the membrane unit.

A second embodiment of the invention is a process, comprising passing a feed stream to a column to produce an overhead stream, flashing the overhead stream to produce a net gas stream and overhead residual stream, a side draw stream and a product stream; passing the overhead residual stream back to the column and dividing the side draw stream to produce a first stream and a second stream; passing the first stream to a stripper to produce a stripper overhead stream and a stripper product stream and passing the second stream to a membrane unit with the stripper overhead stream; passing a retentate stream from the membrane unit back to the stripper and passing a permeate stream from the membrane unit to produce a polymer grade propylene stream. An embodiment of the invention is one, any or all of prior embodiments in this paragraph up through the second embodiment in this paragraph, wherein the feed stream may be a treated liquid petroleum gas stream from a caustic mercaptan oxidation process. An embodiment of the invention is one, any or all of prior embodiments in this paragraph up through the second embodiment in this paragraph, wherein the column comprises about 40 to about 80 trays, preferably about 50 to about 70 trays. An embodiment of the invention is one, any or all of prior embodiments in this paragraph up through the second embodiment in this paragraph, wherein the membrane unit comprises a plurality of membranes wherein the membranes are facilitated transport membranes comprising a nanoporous support membrane, a hydrophilic polymer inside the nanopores on the skin layer surface of the support membrane, a thin, nonporous, hydrophilic polymer layer coated on the surface of the support membrane, and metal salts incorporated in the hydrophilic polymer layer coated on the surface of the support membrane and the hydrophilic polymer inside the nanopores. An embodiment of the invention is one, any or all of prior embodiments in this paragraph up through the second embodiment in this paragraph, wherein the membrane unit operates at about 30-80° C., preferably at about 45-65° C., under 80-300 psig feed pressure, preferably under 100-240 psig feed pressure, with a humidity level at 40-100%, preferably at 50-90%. An embodiment of the invention is one, any or all of prior embodiments in this paragraph up through the second embodiment in this paragraph, wherein the stripper comprises about 15 to about 45 trays, preferably about 20 to about 40 trays. An embodiment of the invention is one, any or all of prior embodiments in this paragraph up through the second embodiment in this paragraph, further comprising the side draw stream back to a treatment unit where contaminants are removed.

A third embodiment of the invention is a process, comprising passing a feed stream to a dividing wall column to produce a first overhead stream, flashing the overhead stream to produce a net gas stream, a side draw stream and a product stream; passing a first portion of the overhead stream back to the column and dividing the second portion of the overhead residual stream to produce a first stream and a second stream; passing a first portion of the side draw stream back to the column and passing the second portion of the side draw stream as a propane product; passing the first stream to a stripper to produce a stripper overhead stream and a stripper product stream and passing the second stream to a membrane unit with the stripper overhead stream; passing a retentate stream from the membrane unit back to the stripper and passing a permeate stream from the membrane unit to a compression and cooling unit to produce a polymer grade propylene stream. An embodiment of the invention is one, any or all of prior embodiments in this paragraph up through the third embodiment in this paragraph, wherein the feed stream may be a treated liquid petroleum gas stream from a caustic mercaptan oxidation process. An embodiment of the invention is one, any or all of prior embodiments in this paragraph up through the third embodiment in this paragraph, wherein the column comprises about 40 to about 80 trays, preferably about 50 to about 70 trays. An embodiment of the invention is one, any or all of prior embodiments in this paragraph up through the third embodiment in this paragraph, wherein the membrane unit comprises a plurality of membranes wherein the membranes are facilitated transport membranes comprising a nanoporous support membrane, a hydrophilic polymer inside the nanopores on the skin layer surface of the support membrane, a thin, nonporous, hydrophilic polymer layer coated on the surface of the support membrane, and metal salts incorporated in the hydrophilic polymer layer coated on the surface of the support membrane and the hydrophilic polymer inside the nanopores. An embodiment of the invention is one, any or all of prior embodiments in this paragraph up through the third embodiment in this paragraph, wherein the membrane unit operates at about 30-80° C., preferably at about 45-65° C., under 80-300 psig feed pressure, preferably under 100-240 psig feed pressure, with a humidity level at 40-100%, preferably at 50-90%. An embodiment of the invention is one, any or all of prior embodiments in this paragraph up through the third embodiment in this paragraph, wherein the stripper comprises about 15 to about 45 trays, preferably about 20 to about 40 trays.

Without further elaboration, it is believed that using the preceding description that one skilled in the art can utilize the present invention to its fullest extent and easily ascertain the essential characteristics of this invention, without departing from the spirit and scope thereof, to make various changes and modifications of the invention and to adapt it to various usages and conditions. The preceding preferred specific embodiments are, therefore, to be construed as merely illustrative, and not limiting the remainder of the disclosure in any way whatsoever, and that it is intended to cover various modifications and equivalent arrangements included within the scope of the appended claims.

In the foregoing, all temperatures are set forth in degrees Celsius and, all parts and percentages are by weight, unless otherwise indicated.

The invention claimed is:

1. A process, comprising:
    passing a feed stream comprising LPG to a column to produce a first overhead stream comprising C3 and a product stream comprising C4;
    passing a first portion of the overhead stream back to the column and splitting a second portion of the overhead stream to produce a first stream and a second stream;
    passing the first stream to a stripper to produce a stripper overhead stream comprising C3 and a stripper product stream comprising propane and passing the second stream to a membrane unit with the stripper overhead stream; and
    passing a retentate stream comprising propane from the membrane unit back to the stripper and passing a permeate stream from the membrane unit to produce a polymer grade propylene stream.

2. The process of claim 1, wherein the feed stream may be a treated liquid petroleum gas stream from a caustic mercaptan oxidation process.

3. The process of claim 1, wherein the column comprises about 40 to about 80 trays.

4. The process of claim 1, wherein the membrane unit comprises a plurality of membranes wherein said membranes are facilitated transport membranes comprising a nanoporous support membrane, a hydrophilic polymer inside nanopores on a skin layer surface of the support membrane, a thin, nonporous, hydrophilic polymer layer coated on the skin layer surface of the support membrane, and metal salts incorporated in the hydrophilic polymer layer coated on the surface of the support membrane and the hydrophilic polymer inside the nanopores.

5. The process of claim 1, wherein the membrane unit operates at about 30-80° C., under 552-2068 kPa (80-300 psig) feed pressure, with a humidity level at 40-100%.

6. A process, comprising:
    passing a feed stream comprising LPG to a column to produce an overhead stream comprising propylene, a side draw stream comprising C3 and a product stream comprising C4, and flashing the overhead stream to produce a net gas stream and an overhead residual stream comprising propylene;
    passing the overhead residual stream back to the column and dividing the side draw stream to produce a first stream and a second stream;
    passing the first stream to a stripper to produce a stripper overhead stream comprising C3 and a stripper product stream comprising propane and passing the second stream to a membrane unit with the stripper overhead stream; and
    passing a retentate stream comprising propane from the membrane unit back to the stripper and passing a permeate stream from the membrane unit to produce a polymer grade propylene stream.

7. The process of claim 6, wherein the feed stream may be a treated liquid petroleum gas stream from a caustic mercaptan oxidation process.

8. The process of claim 6, wherein the column comprises about 40 to about 80 trays.

9. The process of claim 6, wherein the membrane unit comprises a plurality of membranes wherein said membranes are facilitated transport membranes comprising a nanoporous support membrane, a hydrophilic polymer inside nanopores on a skin layer surface of the support membrane, a thin, nonporous, hydrophilic polymer layer coated on the skin layer surface of the support membrane, and metal salts incorporated in the hydrophilic polymer layer coated on the surface of the support membrane and the hydrophilic polymer inside the nanopores.

10. The process of claim 6, wherein the membrane unit operates at about 30-80° C., under 552-2068 kPa (80-300 psig) feed pressure, with a humidity level at 40-100%.

11. The process of claim 6, wherein the stripper comprises about 15 to about 45 trays.

12. A process, comprising:
    passing a feed stream comprising LPG to a dividing wall column to produce a first overhead stream comprising C3, a side draw stream comprising propane and a product stream comprising C4, and flashing the overhead stream to produce a net gas stream and an overhead residual stream comprising propylene and propane;
    passing a first portion of the overhead residual stream back to the column and passing a second portion of the overhead residual stream to a membrane;
    passing a first portion of the side draw stream back to the column and passing the second portion of the side draw stream as a propane product; and
    passing a retentate stream comprising propane from the membrane unit back to the column and passing a permeate stream from the membrane unit to a compression and cooling unit to produce a polymer grade propylene stream.

13. The process of claim 12, wherein the feed stream may be a treated liquid petroleum gas stream from a caustic mercaptan oxidation process.

14. The process of claim 12, wherein the column comprises about 40 to about 80 trays.

15. The process of claim 12, wherein the membrane unit comprises a plurality of membranes wherein said membranes are facilitated transport membranes comprising a nanoporous support membrane, a hydrophilic polymer inside nanopores on a skin layer surface of the support membrane, a thin, nonporous, hydrophilic polymer layer coated on the skin layer surface of the support membrane, and metal salts incorporated in the hydrophilic polymer layer coated on the surface of the support membrane and the hydrophilic polymer inside the nanopores.

16. The process of claim 12, wherein the membrane unit operates at about 30-80° C., under 552-2068 kPa (80-300 psig) feed pressure, with a humidity level at 40-100%.

17. The process of claim 12, wherein the stripper comprises about 15 to about 45 trays.

* * * * *